(12) United States Patent
Perrault et al.

(10) Patent No.: US 7,087,784 B2
(45) Date of Patent: Aug. 8, 2006

(54) PROCESS TO PREPARE OXAZOLIDINONES

(75) Inventors: William R. Perrault, Kalamazoo, MI (US); Bruce Allen Pearlman, Kalamazoo, MI (US); Delara B. Godrej, Kalamazoo, MI (US)

(73) Assignee: Pharmacia & Upjohn, Kalamazoo, MI (US)

( * ) Notice: Subject to any disclaimer, the term of this patent is extended or adjusted under 35 U.S.C. 154(b) by 402 days.

(21) Appl. No.: 10/809,125

(22) Filed: Mar. 25, 2004

(65) Prior Publication Data

US 2004/0220407 A1 Nov. 4, 2004

Related U.S. Application Data

(62) Division of application No. 10/122,852, filed on Apr. 15, 2002.
(60) Provisional application No. 60/285,586, filed on Apr. 20, 2001, and provisional application No. 60/365,581, filed on Mar. 19, 2002.

(51) Int. Cl.
C07C 233/06 (2006.01)

(52) U.S. Cl. ..................................................... 564/224
(58) Field of Classification Search .................. 564/224
See application file for complete search history.

(56) References Cited

U.S. PATENT DOCUMENTS

| | | | | |
|---|---|---|---|---|
| 5,688,792 A | 11/1997 | Barbachyn | ............... | 514/235.5 |
| 5,883,093 A | 3/1999 | Hutchinson | .................. | 514/210 |
| 5,952,324 A | 9/1999 | Barbachyn | .................. | 514/211 |
| 5,968,962 A | 10/1999 | Thomas | ...................... | 514/376 |
| 6,107,519 A * | 8/2000 | Pearlman | .................... | 564/224 |

FOREIGN PATENT DOCUMENTS

| | | |
|---|---|---|
| WO | WO 97/37980 | 10/1997 |
| WO | WO 99/24393 | 5/1999 |
| WO | WO 01/98297 | 12/2001 |

OTHER PUBLICATIONS

JR Gage, et al., "Sterodivergent synthesis of sulfoxide–containing oxazolidinone antibiotics," Tetrahedron Letters, 41 (2000), pp. 4301–4305.

MA Mbappe, et al., "Enzymatic Resolutions in 3–amino–1, 2–propanedial series," Tetrahedron: Asymmetry, 4(5), pp. 1035–1040, 1993.

SE Schaus and Eric N. Jacobsen, "Dyanamic Kinetic Resolution of Epichlorohydren via Enantioselective Catalytic Ring Opening with TMSN,. Practical Synthesis of Aryl Oxazolidinone Antibacterial Agents," Tetrahedron Letters. vol. 37, No. 44, pp. 7937–7940, 1996.

* cited by examiner

*Primary Examiner*—Kamal Saeed
(74) *Attorney, Agent, or Firm*—Lucy X. Yang

(57) ABSTRACT

The present invention relates to a one-step process to prepare pharmacologically active 2-oxo-5-oxazolidinylmethylacetamides.

2 Claims, No Drawings

PROCESS TO PREPARE OXAZOLIDINONES

CROSS-REFERENCE TO RELATED APPLICATIONS

This application is a divisional of non-provisional application U.S. Ser. No. 10/122,852, filed Apr. 15, 2002 which claims the benefit of provisional applications U.S. Ser. No. 60/285,586, filed Apr. 20, 2001 and U.S. Ser. No. 60/365,581, filed Mar. 19, 2002, under 35 USC 119(e)(i), which is incorporated by reference in its entirety.

FIELD OF THE INVENTION

The present invention relates to a one-step process to prepare pharmacologically active 2-oxo-5-oxazolidinylmethylacetamides.

BACKGROUND OF THE INVENTION

The oxazolidinone antibacterial agents are a novel synthetic class of antimicrobials with potent activity against a number of human and veterinary pathogens, including gram-positive aerobic bacteria such as multiply-resistant *staphylococci* and *streptococci,* anaerobic organisms such as *bacteroides* and *clostridia* species, and acid-fast organisms such as *Mycobacterium tuberculosis* and *Mycobacterium avium.*

Various 2-oxo-5-oxazolidinylmethylacetamides are well known to those skilled in the art as pharmacologically useful antibacterials. Various methods are well known to those skilled in the art for preparing these useful therapeutic agents.

For examples, U.S. Pat. No. 5,883,093 discloses azetidine and pyrrolidine phenyloxazolidinones as antibacterial agents and their preparation.

U.S. Pat. No. 5,688,792 discloses oxazine and thiazine phenyloxazolidinones as antibacterial agents and their preparation.

U.S. Pat. No. 5,952,324 discloses bicyclic oxazine and thiazine phenyloxazolidinones as antibacterial agents and their preparation.

U.S. Pat. No. 5,968,962 discloses C—C linked heterocycle phenyloxazolidinones as antibacterial agents and their preparation.

All the preparations referenced above require multiple steps to convert an N-aryl-O-alkylcarbamate to a pharmaceutically active 2-oxo-5-oxazolidinylmethylacetamide. The present invention is a one-step process from N-aryl-O-alkylcarbamates to pharmaceutically active 2-oxo-5-oxazolidinylmethylacetamides. The present invention avoids isolating and purifying intermediates at each multiple step, therefore, it provides for convenient and speedy production of pharmaceutically active 2-oxo-5-oxazolidinylmethylacetamides.

INFORMATION DISCLOSURE

Tetrahedron Letters, Vol. 37, No. 44, pp. 7937–7940 describes the following two-step conversion of A to D:

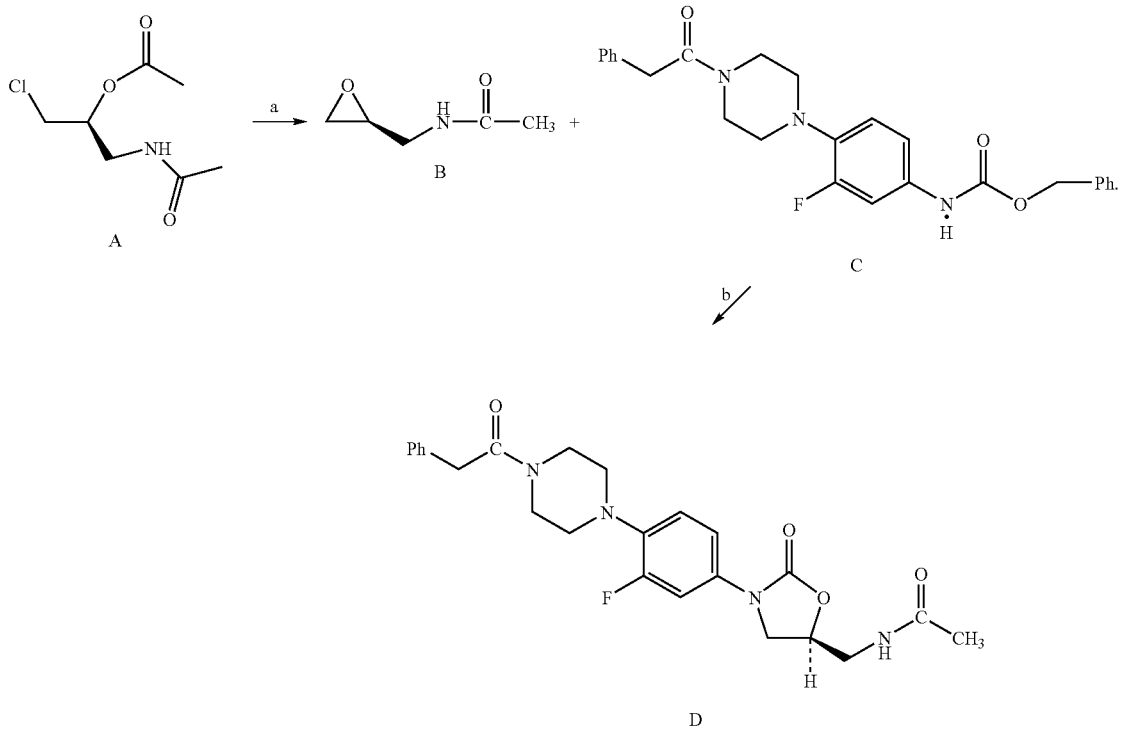

U.S. Pat. No. 6,107,519 discloses the following two-steps reaction from A to F:

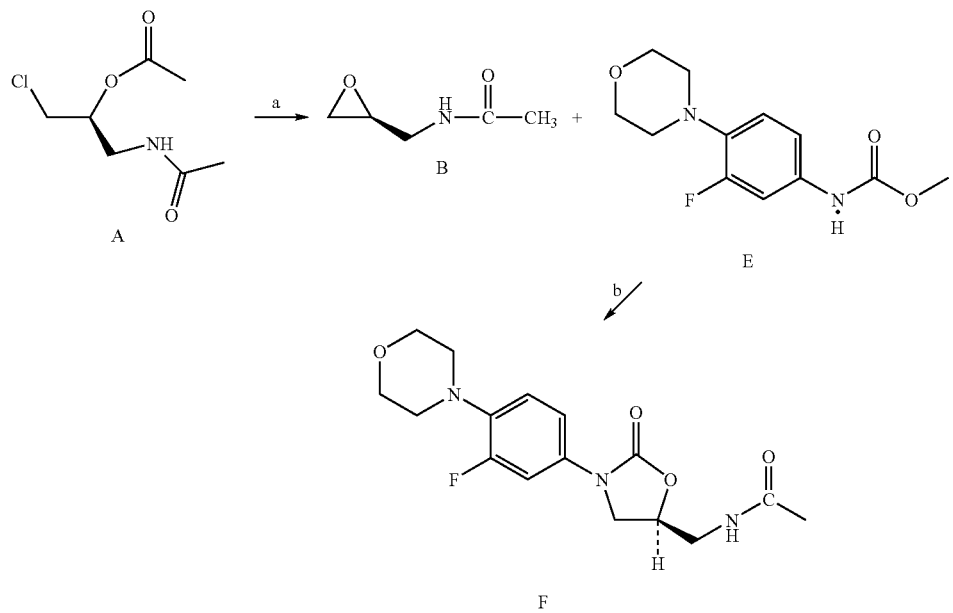

The processes referenced above require two steps from structures A to D or F. they are involved with isolation of structure B, (S) N-oxiranylmethylacetamide, which is an unstable chemical substance and can not be isolated on large scale. Thus, there is unmet need to develop a one-step method for the preparation of pharmaceutically active 2-oxo-5-oxazolidinylmethylacetamides.

SUMMARY OF THE INVENTION

The Present invention is directed to a "one step" method of synthesizing 2-oxo-5-oxazolidinylmethylacetamides. Specifically, the present invention provides a novel method for preparing an (S)-phenyloxazolidinone of formula I

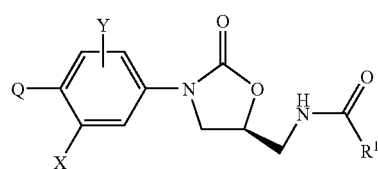

I or a salt thereof, which comprises reacting a N-aryl-O-alkylcarbamate of formula II

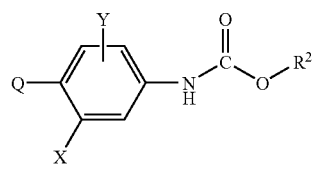

II or a salt thereof, with a compound of formula III

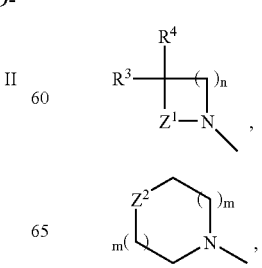

III or a salt thereof, in the presence of a lithium cation, a base and a nucleophile, wherein X and Y are independently H or F;

W1 is Cl, Br, or —OS(O)$_2$—R;

W2 is H or —C(O)—R$_1$;

R is aryl or alkyl, the alkyl optionally being substituted by one or more F, Cl, Br, or I;

R$^1$ is CH$_3$, optionally substituted by one to three fluorine or chlorine atoms;

R$^2$ is cycloalkyl, phenyl, —CH$_2$-phenyl, C$_{2-6}$alkenyl, or C$_{1-12}$alkyl optionally substituted by one to three of F, Br, Cl, —O—C$_{1-6}$alkyl, and NR$^{2a}$R$^{2b}$;

Each R$^{2a}$ and R$^{2B}$ is independently H or C$_{1-4}$alkyl;

Q is structure i, ii, iii, iv, or iv:

i ii

-continued

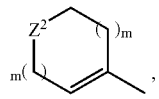
iii

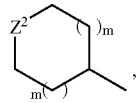
iv

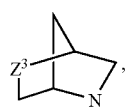
v or Q and X taken together are dihydropyrrolidine, optionally substituted with $R^5$;
$Z^1$ is $CH_2(CH_2)_p$, $CH(OH)(CH_2)_p$, or $C(O)$;
$Z^2$ is S, SO, $SO_2$, O, or $N(R^6)$;
$Z^3$ is S, SO, $SO_2$ or O;
$R^3$ is H or $CH_3$;
$R^4$ is
  a) H,
  b) HO,
  c) $C_{1-3}$alkyl;
  d) $C_{1-4}$alkoxy,
  e) $R^7OCH_2$=C(O)NH—,
  f) $R^8OC(O)NH$—,
  g) $C_{1-3}$alkyl-OC(O)—,
  h) $HOCH_2$—,
  i) $CH_3ONH$,
  j) $CH_3C(O)$—,
  k) $CH_3C(O)CH_2$—,
  l) $CH_3C(OCH_2CH_2O)$—, or
  m) $CH_3C(OCH_2CH_2O)CH_2$—;
$R^3$ and $R^4$ taken together with the carbon atom to which they are attaching form C(O), or C(=$NR^9$);
$R^5$ is
  a) $CH_3C(O)$—,
  b) HC(O)—,
  c) $Cl_2CHC(O)$—,
  d) $HOCH_2C(O)$—,
  e) $CH_3SO_2$—,
  f) $F_2CHC(O)$—,
  g) $H_3CC(O)OCH_2C(O)$—,
  h) $HC(O)OCH_2C(O)$—,
  i) $R^{10}C(O)OCH_2C(O)$—,
  j) $H_3CCHCH_2OCH_2C(O)$—, or
  k) benzyl$OCH_2C(O)$—;
$R^6$ is
  a) H,
  b) $C_{1-6}$alkyl, optionally substituted with one or more OH, CN, or halo,
  c) —$(CH_2)_h$-aryl,
  d) —$COR^{11}$,
  e) —$COOR^{12}$,
  f) —CO—$(CH_2)_h$-$COR^{11}$,
  g) —$SO_2$—$C_{1-6}$alkyl,
  h) —$SO_2$—$(CH_2)_h$-aryl, or
  i) —$(CO)_i$-Het;

$R^7$ is H, $CH_3$, benzyl, or $CH_3C(O)$—;
$R^8$ is $(C_{1-3})$alkyl, aryl, or benzyl;
$R^9$ is
  a) HO—
  b) $CH_3O$—
  c) $H_2N$—
  d) $CH_3OC(O)O$—,
  e) $CH_3C(O)OCH_2C(O)O$—,
  f) aryl-$CH_2OCH_2C(O)O$—,
  g) $HO(CH_2)_2O$—,
  h) $CH_3OCH_2O(CH_2)_2O$—, or
  i) $CH_3OCH_2O$—;
$R^{10}$ is:
  a) $CH_3$—,
  b) $HOCH_2$—,
  c) phenyl-NH—, or
  d) $(CH_3)_2N$—$CH_2$—;
$R^{11}$ is
  a) H,
  b) $C_{1-6}$ alkyl, optionally substituted with one or more OH, CN, or halo,
  c) —$(CH_2)_h$-aryl, or
  d) —$(CH_2)_h$—$OR^{13}$;
$R^{12}$ is
  a) $C_{1-6}$ alkyl, optionally substituted with one or more OH, CN, or halo,
  b) —$(CH_2)_h$-aryl, or
  c) —$(CH_2)_h$—$OR^{13}$;
$R^{13}$ is
  a) H,
  b) $C_{1-6}$alkyl,
  c) —$(CH_2)_h$-aryl, or
  d) —$CO(C_{1-6}$alkyl);
aryl is phenyl, pyridyl or napthyl; at each occurrence, aryl or phenyl may be optionally substituted with one or more F, Cl, Br, I, CN, OH, SH, $C_{1-6}$ alkyl, —$OC_{1-6}$ alkyl, or $SC_{1-6}$alkyl, or $OC(O)CH_3$; het is 5- to 10-membered heterocyclic rings having one or more oxygen, nitrogen, and sulfur atoms; h is 1, 2, 3, or 4; i is 0 or 1; m is 0 or 1; n is 1, 2, or 3; and p is 0, 1, or 2.

Embodiments of this aspect of the invention may include one or more of the following features. $R^1$ is —$CH_3$ or —$CHCl_2$. $R^2$ is methyl, ethyl, propyl, isopropyl, isobutyl, benzyl, 2,2,2-trifluoroethyl, 2-ethoxyethyl, 2-(N,N-dimethylamino)ethyl, 2-(N,N-diethylamino)ethyl, 2,2,2-trichloroethyl, isopropenyl, phenyl, p-tolyl, 2-methoxyphenyl, or 4-methoxyphenyl. Q is structure ii. Q is structure iii or iv. $Z^2$ is O or $SO_2$. $Z^2$ is $N(R^6)$. $R^6$ is $COR^{11}$. $R^{11}$ is $C_{1-6}$alkyl optionally substituted with one or more OH. The base has $pK_{DMSO}$ greater than 12. The base is alkoxide, $C_{1-4}$alkycarbanion, conjugate base of a carbamate, 1,8-diazabicyclo[5.4.0]undec-7-ene, 1,5-diazabicyclo[4.3.0] non-5-ene, lithium diisopropylamide, lithium dicyclohexylamide, lithium hexamethyldisilazide, or lithium amide. The base is alkoxide having one to five carbon atoms. The base is tertiary-amylate. The base is tertiary-butoxide. The nucleophile is alkoxide. The nucleophile is methoxide, ethoxide, isopropoxide, isobutoxide, 2-ethoxyethyl, 2-(N,N-dimethylamino)ethoxide, 2,2,2-trichloroethoxide, or 2,2,2-trifluoroethoxide. W1 is Cl. W1 is Br. W1 is —OS(O)$_2$—R. W2 is H. W2 is —C(O)—$R_1$. The process is conducted in a solvent system comprising THF and acetonitrile. The process is conducted in a solvent system comprising DMF.

The present invention also provides novel intermediates.

The intermediate of formula IV is useful in the method for preparing an (S)-phenyloxazolidinone of formula I described above

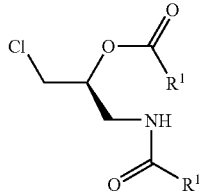

IV wherein $R^1$ is $CHCl_2$, $CHBr_2$, $CH_2Cl$, $CH_2Br$, $CCl_3$, $CBr_3$, $CHF_2$, $CHF_2$, or $CF_3$.

The intermediate of the formula V is also useful in the method for preparing an (S)-phenyloxazolidinone of formula I described above

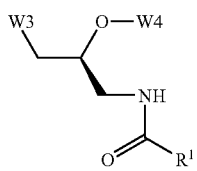

V wherein
W3 is —OS(O)$_2$—R;
W4 is H or —C(O)—R1;
R is aryl or alkyl, the alkyl optionally being substituted by one or more F, Cl, Br, or I, and the aryl optionally being substituted with one or more F, Cl, Br, I, CN, $NO_2$, OH, SH, $C_{1-6}$alkyl, $OC_{1-6}$alkyl, or $SC_{1-6}$alkyl, or $OC(O)CH_3$; and
$R^1$ is $CH_3$, optionally substituted by one to three fluorine or chlorine atoms.

DETAILED DESCRIPTION OF THE INVENTION

As used herein, the terms and phrases have the meanings, definitions, and explanations known in the art. Some of the more commonly used phrases are described in more detail below.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

Alkyl refers to both to straight and branched groups; but reference to an individual radical such as "propyl" embraces only the straight chain radical, whereas specific reference to "isopropyl" embraces only the branched chain isomer. When alkyl can be partially unsaturated, the alkyl chain may comprise one or more (e.g. 1, 2, 3, or 4) double or triple bonds in the chain.

Alkenyl refers to a both to straight and branched alkyl groups containing one or more double bonds in the carbon chain.

Cycloalkyl refers to a three to seven cycloalkyl ring system.

Alkoxy refers to a —O-alkyl group wherein alkyl is a straight or branched alkyl group.

Aryl refers to phenyl, pyridyl or naphthyl, which may be optionally substituted with one or more F, Cl, Br, I, CN, OH, SH, $C_{1-6}$ alkyl, $OC_{1-6}$ alkyl, or $SC_{1-6}$ alkyl, or —OC(O)CH$_3$.

Halogen or halo refers to fluorine, chlorine, bromine, and iodine.

The term "het" refers to 5 to 10 membered heterocyclic rings containing one or more oxygen, nitrogen, and sulfur atoms forming such groups as, for example, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 4,5,-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl, 1-purinyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-dithiazolone. Each of these moieties may be substituted as appropriate.

It should be noted that starting with an (S)-acetamidoacetoxypropane of formula III yields a pharmaceutically active (S)-2-oxo-5-oxazolidinylmethylacetamide of formula I. If the process of the present invention begins with a racemic form, the product obtained is the corresponding racemic form.

A preferred embodiment of a compound of formula I or III is wherein $R^1$ is a methyl group.

Another preferred embodiment of a compound of formula I or III is wherein $R^1$ is dichloromethyl group.

Another preferred embodiment of a compound of formula I or II is wherein Q is structure ii.

A more preferred embodiment of a compound of formula I or II is wherein Q is structure ii and $Z^2$ is O.

A more preferred embodiment of a compound of formula I or II is wherein Q is structure ii and $Z^2$ is $SO_2$.

Another preferred embodiment of a compound of formula I or II is wherein Q is structure iii.

Another preferred embodiment of a compound of formula I or II is wherein Q is structure iv.

Another preferred embodiment of a compound of formula I or II is wherein Q is a structure ii, iii, or iv, wherein $Z^2$ is $N(R^6)$, wherein $R^6$ is $COR^{11}$, wherein $R^{11}$ is $C_{1-6}$alkyl optionally substituted with one or more OH.

Another preferred embodiment of a compound of formula II is wherein $R_2$ is isobutyl.

Another preferred embodiment of a compound of formula II is wherein $R_2$ is benzyl.

Scheme I illustrates the general synthetic procedure for the preparation of pharmaceutically active 2-oxo-5-oxazolidinylmethylacetamides.

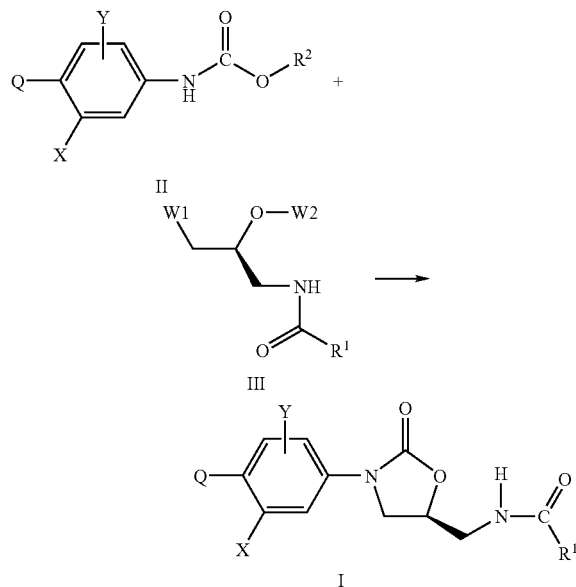

SCHEME I

As shown in Scheme I, reacting a carbamate of formula II with an (S)-acetamidoacetoxypropane of formula III provides the corresponding (S)-2-oxo-5-oxazolidinylmethylacetamide of formula I, wherein W1, W2, $R^1$, $R^2$, Q, X and Y are the same as defined previously or as in the claims. The reaction occurs in the presence of a base, a lithium cation, a nucleophile and a solvent. The identity of the base is not critical as long as the base is capable of deprotonating carbamate of formula II such as a base whose conjugate acid has a $pK_{DMSO}$ greater than about 12. The term "$pK_{DMSO}$" means that a base's pK value is determined in dimethyl sulfoxide. Examples of the bases which can be used in the present invention are: an alkoxide group having one through seven carbon atoms; a $C_{1-4}$ alkyl carbanion such as a methyl, sec-butyl, butyl or t-butyl carbanion; a conjugate base of a carbamate; 1,8-diazabicyclo[5.4.0]undec-7-ene (DBU); 1,5-diazabicyclo[4.3.0]non-5-ene (DBN); lithium diisopropylamide; lithium dicyclohexylamide; lithium hexamethyldisilazide; and, lithium amide. A preferred base is an alkoxide group having four or five carbon atoms, particularly t-amylate or t-butoxide.

The most preferred bases contain a lithium cation and an alkoxide group such as lithium t-amylate or lithium t-butoxide. In such cases, the lithium cation and the base required by the present invention may be from the same chemical substance.

Where a base does not contain a lithium cation (for example, a base is a sodium, potassium, or tetra-alkylammonium salt), mixing such base with a lithium salt, such as lithium chloride, lithium bromide, lithium iodide, lithium acetate, lithium tetrafluoroborate, and other lithium inorganic salts, can be used to form the lithium cation and base in situ.

The identity of the nucleophile also is not critical as long as it is capable of displacing the acetate from (S)-acetamidoacetoxypropane of formula III. An example of a nucleophile is an alkoxide group, linear or branched, having one through seven carbon atoms. A preferred nucleophile is methoxide, ethoxide, isopropoxide, isobutoxide, 2-ethoxyethyl, 2-(N,N-dimethylamino)ethoxide, 2,2,2-trichloroethoxide, or 2,2,2-trifluoroethoxide. Commercial alkoxide salts such as lithium, sodium or potassium methoxide, ethoxide or isopropoxide can be used or the alkoxide may be formed in situ by reacting a base, as referenced above, with a corresponding alcohol such as methanol, ethanol, or isopropanol. Where a lithium alkoxide is used as a nucleophile and a base, the lithium cation, the base and the nucleophile required by the present invention may be from the same chemical substance, and at least two (2) equivalents of such chemical substance are needed for the reaction.

Examples of a solvent are: ethers such as tetrahydrofuran and glyme; amides such as dimethylformamide (DMF) and dimethylacetamide (DMAc); acetonitrile; alcohols such as t-amyl alcohol and t-butyl alcohol; and chlorinated solvents such as methylene chloride. Hydrocarbon cosolvents such as toluene, heptane, hexane, isooctane and petroleum ethers, e.g. branched octanes, can be used as well. The choice of solvent is related to the solubility of carbamate of formula II and (S)-acetamidoacetoxypropane of formula III, and can be determined easily by those skilled in the art. The solvent may be a solvent system which includes two or more solvents. Unexpectedly a co-solvent system including THF and acetonitrile permits dissolution of higher concentrations of carbamates of formula II and (S)-acetamidoacetoxypropanes of formula III relative to reactions utilizing THF and acetonitrile alone. Increasing the concentration of dissolved starting material increases the amount of isolated product.

All of the above referenced lithium salts, bases, nucleophiles and solvents are commercially available.

The starting material, carbamates of formula II, can be prepared according to the procedures well known in the art, specifically, they can be prepared according to the procedures described in U.S. Pat. Nos. 5,883,093, 5,688,792, 5,952,324, and 5,968,962, incorporated herein by reference in their entirty.

The starting material of formula II, can be prepared according to the Scheme II utilizing different equivalents of the acid anhydride of formula B as well as procedures described in Tetrahedron Letters, Vol. 37, No. 44, pp. 7937–7940 and WO 9924393. (S)—N-(3-bromo-2-hydroxypropyl)-acetamide and (S)—N-(2-acetoxy-3-bromopropyl)-acetamide are commercially available from Samsung Fine Chemicals.

SCHEME II

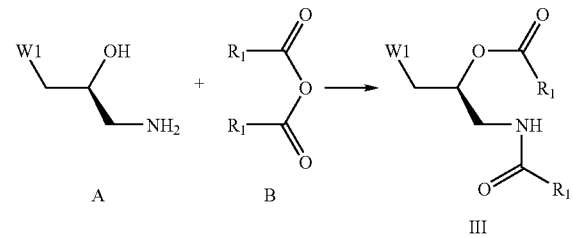

Where each methyl group of a compound of formula III is substituted by one, two, or three halogen atoms, it can be obtained by reacting a compound of formula A with chloroacetic anhydride, dichloroacetic anhydride, trichloroacetic anhydride, fluoroacetic anhydride, and etc. All these reagents are commercially available. Compounds of formula III substituted by one, two, or three halogen atoms are novel compounds.

Definitions

All temperatures are in degrees Centigrade.

TLC refers to thin-layer chromatography.

HPLC refers to high pressure liquid chromatography.

THF refers to tetrahydrofuran.

DMF refers to dimethylformamide.

DMAC refers to dimethylacetamide.

Chromatography (column and flash chromatography) refers to purification/separation of compounds expressed as (support, eluent). It is understood that the appropriate fractions are pooled and concentrated to give the desired compound(s).

IR refers to infrared spectroscopy.

CMR refers to C-13 magnetic resonance spectroscopy, chemical shifts are reported in ppm (δ) downfield from TMS.

NMR refers to nuclear (proton) magnetic resonance spectroscopy, chemical shifts are reported in ppm (δ) downfield from tetramethylsilane.

MS refers to mass spectrometry expressed as m/e, m/z or mass/charge unit. [M+H]$^+$ refers to the positive ion of a parent plus a hydrogen atom. EI refers to electron impact. CI refers to chemical ionization. FAB refers to fast atom bombardment.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

(S)—N-[2-(acetyloxy)-3-chloropropyl]acetamide

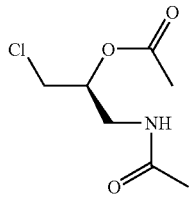

To a slurry of (S)-1-amino-3-chloro-2-propanol hydrochloride (500 g, 3.43 mol) in methylene chloride (1.54 kg) and acetic anhydride (803 g, 7.87 mol) is added pyridine (340 g, 4.3 mol) over 1 h while maintaining 38 to 46° C. The mixture is then stirred at 21 to 46° C. for 22 h. Water (600 ml) is added at 22 to 24° C. then aqueous potassium carbonate (47 wt %, 2.0 kg, 6.80 mol) while maintaining 6 to 11° C. Water (600 ml) and methylene chloride (600 ml) are added and the phases separated at 24° C. The aqueous is washed with methylene chloride (600 ml) and the combined organics concentrated under reduced pressure to 1.3 liter total volume. Toluene (2×1.0 liter) was added and the mixture concentrated to 1.4 liter after each addition. The mixture is cooled to 24° C. and isooctanes (2.3 liter) added. The resultant slurry is cooled to 0° C. and the precipitate collected by vacuum filtration, washed with isooctanes (700 ml) and dried in a nitrogen stream to give the title compound. This compound can also be prepared according to the procedures disclosed in WO 9924393 or Tetrahedron Letters, Vol. 37, No. 44, pp. 7937–7940.

$^1$H NMR (400 MHz, CDCl$_3$) δ 2.00, 2.12, 3.50, 3.60, 3.70, 5.09, 6.05; MS (CI) m/z 194 (M+H, $^{35}$Cl, 100), 196 (M+H, $^{37}$Cl, 34); Anal calcd for C$_7$H$_{12}$ClNO$_3$: C, 43.42; H, 6.25; N, 7.23; found C, 43.36; H, 6.34; N, 7.36; [α]$^{25}_D$=−9 (C 0.87, methylene chloride).

Example 1

(S)—N-[[3-(3-fluoro-4-morphoninylphenyl)-2-oxo-5-oxazolidinyl]methyl]acetamide

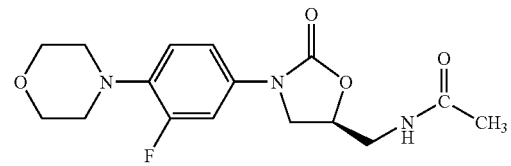

A Dimethylformamide as Solvent.

To a solution of N-carbobenzoxy-3-fluoro-4-morpholinylaniline (1.032 g, 3.125 mmol) in N,N-dimethylformamide (2.0 ml) and methanol (0.202 g, 6.32 mmol, 2.02 eq) at 20° C. is added a solution of lithium t-butoxide in THF (4.16 g of an 18.1 wt % solution, 9.39 mmol, 3.00 eq) while keeping less than 24° C. with an ice bath. The solution is cooled to 5° C. and (S)—N-[2-(acetyloxy)-3-chloropropyl]acetamide (1.207 g, 6.234 mmol, 2.00 eq) is added. The resulting solution is allowed to stand at 21° C. for 21 hours at which point HPLC showed an 86.8% conversion. Saturated aqueous ammonium chloride (5.0 ml) is added followed by water (30 ml), saturated aqueous sodium chloride (20 ml) and methylene chloride (20 ml). The phases are separated and the aqueous washed with methylene chloride (3×20 ml). The organics are dried on magnesium sulfate and concentrated to an oil in vacuo (4.209 g). Xylenes A.R. (25 ml) is added and the product is crystallized by seeding and sonicating. The product is collected by vacuum filtration, washed with xylenes A.R. (10 ml) and dried in a nitrogen stream to afford the title compound (0.6509 g, 61.8%). The filtrate is concentrated in vacuo to an oil and xylenes (15 ml) added. The second crop is crystallized by seeding and sonicating. The product is collected by vacuum filtration, washed with xylenes A.R. (10 ml) and dried in a nitrogen stream to afford the title compound (0.1085 g, 10.3%).

$^1$H NMR (CDCl$_3$, 400 MHz) δ 7.43, 7.07, 6.91, 6.43, 4.77, 4.02, 3.86, 3.76, 3.66, 3.05, 2.02; MS (EI) m/z (relative intensity) 337 (90), 293 (81), 209 (100); Anal Calcd for C$_{16}$H$_{20}$FN$_3$O$_4$: C, 56.97; H, 5.97; N, 12.46; found: C, 56.86; H, 6.05; N, 12.44; [α]$^{25}_D$=−16 (C 1.05, ethanol).

B THF as Solvent

To N-carbobenzoxy-3-fluoro-4-morpholinylaniline (5.006 g, 15.15 mmol) and lithium t-butoxide (3.621 g, 45.23 mmol, 2.99 eq) is added THF (15 ml) yielding a beige solution after a moderate exotherm from 24 to 31° C. The mixture is cooled to 14° C. and methanol (0.9691 g, 30.25 mmol, 2.00 eq) added with an exotherm to 20° C. The resulting solution is cooled to 7° C., yielding a thick slurry. (S)—N-[2-(acetyloxy)-3-chloropropyl]acetamide (5.885 g, 30.39 mmol, 2.01 eq) is added and the mixture stirred at 15 to 18° C. for 15 h. Acetic acid (1.73 ml, 30.22 mmol, 2.00 eq) is added with an exotherm from 13 to 27° C., followed by water (20 ml) and methylene chloride (20 ml). The phases are separated and the aqueous washed with methylene chloride (2×10 ml). The combined organics are dried on magnesium sulfate then concentrated in vacuo to a net weight of 18 g. The resulting oil is seeded and ethyl acetate (28 g) added to yield a thin slurry. The slurry is concentrated to 29 g and ethyl acetate (30 g) added. The slurry is cooled to −25° C. and the product collected by vacuum filtration, washed with −25° C. ethyl acetate (2×5 ml) and dried in a nitrogen stream to give the title compound (3.725 g, 72.9%): HPLC retention time 1.60 min conditions: Inertsil ODS-2 5.0 micron 150×4.6 mm, flow rate=2.0 ml/min, gradient elution from 40:60 A:B to 80:20 A:B over 10 minutes; A=acetonitrile; B=water.

Example 2

(+/−)N-[[3-fluoro-4-(4-morpholinyl)phenyl]-2-oxo-5-oxazolidinyl]methyl]acetamide

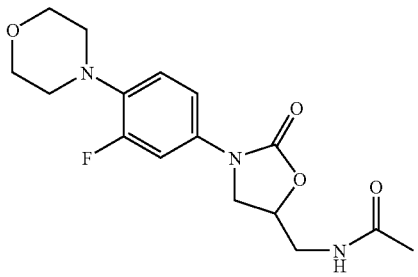

A Dimethylformamide as Solvent.

To a solution of 1-acetamido-2-hydroxy-3-chloropropane (0.879 g, 5.80 mmol) in DMF (1.0 ml) at −40° C. is added lithium t-butoxide (0.4620 g, 5.77 mmol), followed by N-benzyloxy-3-fluoro-4-morpholinylaniline (2.013 g, 6.09 mmol), lithium t-butoxide (0.4671 g, 5.84 mmol) and DMF (2 ml). The mixture was warmed to 20° C. and stirred for 22 h. HPLC [stationary phase is 4.6×250 mm Zorbax RX-C8 column; mobile phase is acetonitrile (650 ml), triethylamine (1.85 ml), acetic acid (1.30 ml) and water of sufficient amount to make 1000 ml; flow rate=3.0 ml/min; UV detection at 254 nm] showed the major component to be the title compound (Rt=0.95 min).

B Dimethylacetamide as Solvent

To a solution of N-carbobenzoxy-3-fluoro-4-morpholinylaniline (0.1315 g, 0.3981 mmol) and lithium ethoxide (0.0817 g, 1.571 mmol 3.95 eq) in N,N-dimethylacetamide (0.60 ml) is added N-[2-(acetyloxy)-3-chloropropyl]acetamide (0.0760 g, 0.3925 mmol, 0.99 eq). The mixture is stirred at room temperature 23.5 h to give the title compound: Silica gel TLC $R_f$=0.46 (10% methanol/methylene chloride).

Example 3

(S)—N-[[3-[4-(3,6-dihydro-2H-thiopyran-4-yl)-3-fluorophenyl]-2-oxo-5-oxazolidinyl]methyl]acetamide

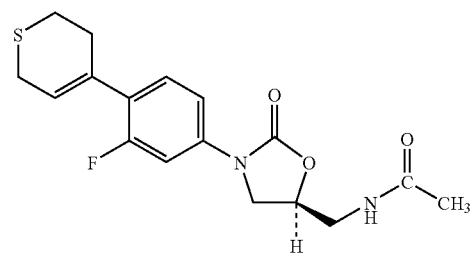

To a mixture of [4-(3,6-dihydro-2H-thiopyran-4-yl)-3-fluorophenyl]carbamic acid 2-methylpropyl ester (17.89 g, 57.83 mmol), (S)—N-[2-(acetyloxy)-3-chloropropyl]acetamide (22.35 g, 115.42 mmol, 2.00 eq), methanol (3.66 g, 114 mmol, 1.97 eq), 2,6-di-tert-butyl-4-methylphenol (0.1365 g, 0.6194 mmol, 0.0107 eq), toluene (52 ml), isooctanes (49 ml), and N,N-dimethylformamide (34.3 ml) is added a solution of lithium t-butoxide (13.94 g, 174.1 mmol, 3.01 eq) in isooctanes (130 ml) over 1.6 h while maintaining 15° C. Isooctanes (20 ml) is added and the mixture stirred at 15 to 19° C. for 17 h. The mixture is cooled to 0° C. and acetic acid (6.7 ml, 117 mmol, 2.02 eq) added. The mixture is warmed to 21° C. and methanol (29 ml) added. The phases are separated and the upper washed twice with a mixture of methanol (29 ml) and water (9 ml). To the combined lower phases is added water (69 ml) and methylene chloride (69 ml). The phases are separated and the upper phase washed twice with methylene chloride (29 ml). The combined lower phases are concentrated under reduced pressure to 112 ml total volume. Methanol (69 ml) is added and the mixture concentrated to 112 ml. Methanol (69 ml) is added and the mixture concentrated to 75 ml then toluene (65 ml) is added. Water (65 ml) is added over ½ h while maintaining 19 to 30° C. The mixture is cooled to 9° C. and isooctanes (56 ml) added. The slurry is cooled to 0° C. and the precipitate collected by vacuum filtration, washed with water (22 ml) and isooctanes (22 ml) and dried in a nitrogen stream to give the title compound (15.909 g, 78.5%): HPLC retention time=2.77 min (column=Phenomenex Luna 5.0 micron C-8(12) 150×4.6 mm, flow rate=2.0 ml/min, gradient elution from 40:60 A:B to 73.3:26.7 A:B over 15 minutes; A=acetonitrile; B=water).

$^1$H NMR (400 MHz, CDCl$_3$) δ 2.02, 2.62, 2.85, 3.32, 3.68, 3.79, 4.04, 4.797, 6.01, 6.56, 7.12, 7.19, 7.37; MS (EI) m/z 350 (M+, 100); Anal. Calcd for C$_{17}$H$_{19}$FN$_2$O$_3$S: C, 58.27; H, 5.47; N, 7.99; Found: C, 58.18; H, 5.51; N, 7.92.

Example 4

(S)—N-[[3-(3-fluorophenyl)-2-oxo-5-oxazolidinyl]methyl]acetamide

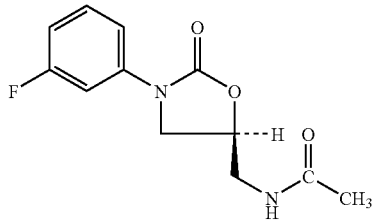

To a mixture of 3-fluorophenylcarbamic acid 2-methylpropyl ester (300.0 g, 1.42 mol), (S)—N-[2-(acetyloxy)-3-chloropropyl]acetamide (556.1 g, 2.87 mol, 2.02 eq), methanol (90.03 g, 2.81 mol, 1.98 eq) and N,N-dimethylformamide (500 ml) is added a slurry of lithium t-amylate (401.3 g, 4.27 mol, 3.00 eq) in heptane (1 liter) while maintaining −4 to 7° C., followed by heptane (100 ml). The mixture is then stirred at 19 to 20° C. for 21 h. The reaction mixture is then added to a mixture of ammonium chloride (228 g, 4.26 mol, 3.00 eq), water (2.0 liter) and toluene (1.0 liter) while maintaining 8 to 10° C. The reaction mixture is rinsed in with a mixture of water (100 ml), saturated ammonium chloride (50 ml) and toluene (100 ml). The precipitate is collected by vacuum filtration and washed with heptane (1 liter) and water (1 liter) and dried in a nitrogen stream to give 252.4 g of crude product. This is triturated in acetonitrile (1 kg) at 90° C. and the slurry concentrated under reduced pressure to 800 ml total volume. Toluene (1900 ml) is added while concentrating to maintain 800 ml total volume. Water (1 liter) and heptane (1 liter) are added and the precipitate collected by vacuum filtration, washed with water (750 ml) and heptane (250 ml) and dried in a nitrogen stream to give the title compound (225.7 g, 63.0%).

$^1$H NMR (400 MHz, CDCl$_3$) δ 1.84, 3.35, 3.43, 3.76, 4.13, 4.75, 6.96, 7.31, 7.43, 7.50, 8.25; Anal Calcd for C$_{12}$H$_{13}$FN$_2$O$_3$: C, 57.14; H, 5.19; N, 11.11; found: C, 56.99; H, 5.21; N, 11.09; $[\alpha]^{25}_D$=−40 (C 1.05, acetonitrile). A second crop is collected from the filtrates which gave additional title compound (46.8 g, 13.1%, total yield=76.1%)

Example 5

N-[[(5S)-3-[4-(1,1-Dioxido-4-thiomorpholinyl)-3,5-difluorophenyl]-2-oxo-5-oxazolidinyl]methyl]acetamide

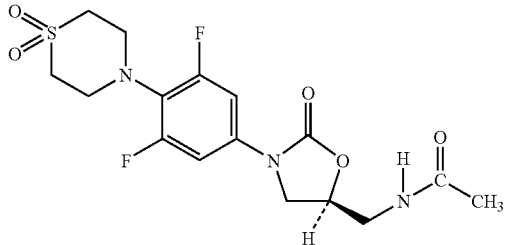

A THF as Solvent

A slurry of lithium t-butoxide (18.0 g, 223.5 mmol, 3.00 eq) in THF (100 ml) is prepared. Isobutyl 4-(1,1-dioxido-4-thiomorpholinyl)-3,5-difluorophenylcarbamate (27.0 g, 74.5 mmol) is dissolved in THF (180 ml) then added to the lithium t-butoxide slurry while maintaining less than 20° C. The mixture is stirred for 15 min then methanol (6.1 ml, 149 mmol, 2.0 eq) is added. (S)—N-[2-(acetyloxy)-3-chloropropyl]acetamide (28.9 g, 149 mmol, 2.0 eq) is dissolved in THF (100 mL) and added to the reaction mixture over 1 h while maintaining the reaction temperature between 15 and 17° C. The cloudy light yellow/brown solution is stirred at 15 to 16° C. for 16 h. The reaction is then quenched with concentrated acetic acid (8.6 ml, 149 mmol, 2.0 eq) while maintaining less than 20° C. Water (75 ml) is added via addition funnel over 3 min. The phases are separated and the organic phase washed with water (20 ml). The organic phase is concentrated to approximately 200 ml total volume. Isopropanol (300 ml) is added slowly to the stirred orange solution via syringe pump at a rate of 2 ml/min. The yellow slurry is then cooled to approximately 5 to 10° C. and stirred for 30 min. The product is collected by vacuum filtration, washed with cold isopropanol (2×100 ml) and dried in vacuo at 60° C. overnight to give the title compound (22.0 g, 73%): HPLC retention time=3.0 min (99.8 area %); HPLC procedure: Inertsil ODS-2 5.0 micron 150×4.6 mm, flow rate=1.0 ml/min, detection at 254 nm, isocratic elution solvent: 479.5 g buffer (1 l water, 1.57 g ammonium formate, formic acid to pH=3.2) and 409.1 g acetonitrile.

B Mixture of THF and Acetonitrile as Solvent

To a mixture of isobutyl 4-(1,1-dioxido-4-thiomorpholinyl)-3,5-difluorophenyl carbamate (100 g, 276 mmol), (S)—N-[2-acetyloxy-3-chloropropyl]acetamide (106.8 g, 552 mmol, 2.0 eq), THF (60 ml), methanol (17.7 g, 552 mmol, 2.0 eq) and acetonitrile (200 ml) is added lithium t-butoxide (66.3 g, 828 mmol, 3.0 eq) and THF (140 ml) over 2 h while maintaining less than 5° C. The mixture is stirred at 14 to 18° C. for 20 h and acetic acid (33.1 g, 552 mmol, 2.0 eq) is added while maintaining less than 20° C. HPLC indicated>90% conversion to the title compound (retention time 1.8 min): HPLC procedure: Inertsil ODS-2 5.0 micron 150×4.6 mm, flow rate=2.0 ml/min, detection at 229 nm, gradient elution from 40:60 acetonitrile: water to 80:20 acetonitrile: water over 10 min. The reaction mixture was cooled to 7° C. and acetic acid (33.1 g, 552 mmol, 2.0 eq) was added. Water (550 ml) was added and the mixture concentrated in vacuo to 800 ml total volume. THF (50 ml), methanol (300 ml) and toluene (600 ml) were then added and the phases separated at 60–65° C. The upper phase was washed with a mixture of methanol (100 ml) and water (400 ml) and the combined lower phases washed with toluene (600 ml). The toluene wash was backextracted with a mixture of water (400 ml) and methanol (100 ml). The combined lower phases were concentrated in vacuo to 1.8 L and extracted with methylene chloride (3×500 ml). The combined extracts were concentrated in vacuo to 1000 ml. Water (1600 ml) was added and the mixture concentrated to 1500 total volume. Methanol (600 ml) was added and the mixture concentrated to 2000 ml total volume at 75° C. The slurry was cooled to 0° C. and the precipitate collected by vacuum filtration, washed with cold water (1000 ml) and dried in 60° C. vacuum oven to give the title compound (91.1 g, 81.8%).

Unexpectedly co-solvent systems including THF and acetonitrile permit dissolution of higher concentrations of starting material relative to reactions utilizing THF and acetonitrile alone. Increasing the concentration of dissolved starting material increases the amount of isolated product. Advantageously, the THF/acetonitrile co-solvent system boils at low temperatures such that the product can be isolated in large-scale production at a cheaper cost and safer reaction condition relative to higher boiling solvent systems such as DMF.

C Acetonitrile as Solvent

To a mixture of isobutyl 4-(1,1-dioxido-4-thiomorpholinyl)-3,5-difluorophenyl carbamate (5.0 g, 14 mmol), (S)—N-[2-(acetyloxy)-3-chloropropyl]acetamide (5.4 g, 28 mmol, 2.0 eq), methanol (0.88 g, 28 mmol, 2.0 eq) and acetonitrile (17 ml) is added lithium t-butoxide (3.3 g, 41 mmol, 3.0 eq) and acetonitrile (18 ml) while maintaining less than 5° C. The mixture is stirred at 15 to 23° C. for 1 day. HPLC indicated conversion to the title compound (retention time 1.8 min): HPLC procedure: Inertsil ODS-2 5.0 micron 150×4.6 mm, flow rate=2.0 ml/min, detection at 229 nm, gradient elution from 40:60 acetonitrile: water to 80:20 acetonitrile: water over 10 min.

D Methylene Chloride, Methylene Chloride and Acetonitrile or Methylene Chloride and THF as Solvent Following the procedure of the previous example and making non-critical variations, but substituting a mixture of methylene chloride and acetonitrile, a mixture of methylene chloride and THF, or DMF for acetonitrile, HPLC indicated conversion to the title compound (retention time 1.8 min): HPLC procedure: Inertsil ODS-2 5.0 micron 150×4.6 mm, flow rate=2.0 ml/min, detection at 229 nm, gradient elution from 40:60 acetonitrile: water to 80:20 acetonitrile: water over 10 min.

E Lithium Diisopropylamide as Base

Following the procedures of example 4 and making non-critical variations, but substituting lithium diisopropylamide (1 eq), and potassium t-butoxide (2 eq) for lithium t-butoxide, HPLC indicated formation of the title compound (retention time 1.7 min): HPLC procedure: Inertsil ODS-2 5.0 micron 150×4.6 mm, flow rate=2.0 m/min, detection at 229 nm, gradient elution from 40:60 acetonitrile: water to 80:20 acetonitrile: water over 10 min.

Example 6

(S)—N-[[3-(3-fluoro-4-morphoninylphenyl)-2-oxo-5-oxazolidinyl]methyl]acetamide (ethoxide or isopropoxide as nucleophile)

Following the procedures of example 1 and making non-critical variations, but substituting ethanol (2 eq) or isopropanol (2 eq) for methanol, HPLC indicated formation of the title compound (retention time 0.9 min): Inertsil ODS-2 5.0 micron 150×4.6 mm, flow rate=2.0 ml/min, gradient elution from 40:60 A:B to 80:20 A:B over 10 minutes; A=acetonitrile; B=water.

Example 7

N-[[(5S)-3-[4-(1,1-Dioxido-4-thiomorpholinyl)-3,5-difluorophenyl]-2-oxo-5-oxazolidinyl]methyl]acetamide (acetonitrile as solvent)

Following the procedures of example 5C and making non-critical variations, but substituting sodium methoxide (2 eq) for lithium t-butoxide (2 eq) and methanol (2 eq), HPLC indicated formation of the title compound (retention time 1.7 min): HPLC procedure: Inertsil ODS-2 5.0 micron 150×4.6 mm, flow rate=2.0 ml/min, detection at 229 nm, gradient elution from 40:60 acetonitrile: water to 80:20 acetonitrile: water over 10 min.

Example 8

N-[[(5S)-3-[4(1,1-Dioxido-4-thiomorpholinyl)-3,5-difluorophenyl]-2-oxo-5-oxazolidinyl]methyl]acetamide.

1) With (S)—N[2-(acetyloxy)-3-bromopropyl]acetamide

Isobutyl 4-(1,1-dioxido-4-thiomorpholinyl)-3,5-difluorophenylcarbamate (2.5 g, 6.9 mmol) and (S)—N[2-(acetyloxy)-3-bromopropyl]acetamide (3.27 g, 13.8 mmol, 2.0 eq) and methanol (0.56 ml, 13.8 mmol, 2.0 eq.) are stirred in acetonitrile (5 ml). A slurry of lithium t-butoxide (1.7 g, 20.7 mmol, 3.0 eq) in THF (5 ml) is prepared and added to the carbamate/acetamide mixture while maintaining a temperature less than 20° C. The cloudy light yellow/brown solution is stirred at 15–16° C. for 16 h. The reaction is quenched with a solution of concentrated acetic acid (0.8 ml, 13.6 mmol, 2.0 eq) in THF (1.8 ml) while maintaining a temperature less than 20° C. Water (7 ml) is added to the mixture. The mixture is concentrated to approximately 20 ml volume and washed with toluene (15 ml) and methanol (7 ml) while maintaining temperature above 60° C. The phases are separated and the upper layer is washed twice with a mixture of water (20 ml) and methanol (5 ml) while maintaining temperature above 60° C. Combined lower phases are washed twice with methylene chloride (2×20 ml). The combined lower phases are concentrated to approximately 25 ml volume and water (35 ml) is added. The slurry is concentrated to approximately 45 ml volume and slowly cooled to 0° C. The precipitate is collected by vacuum filtration, washed with a cold solution of water (10 ml) and methanol (2.5 ml) and dried in a nitrogen stream to give the title compound (2.32 g., 83%). HPLC retention time=1.83 mins (column=Phenomenex IB-SL Phenyl BD, 150 mm×4.6 mm, flow rate–1.0 ml/min, detection at 254 nm, isocratic elution solvent: 350 ml acetonitirile and 650 ml TEAP pH 3.6 (TEAP pH 3.6=0.7 ml triethylamine in 1 L water adjusted to pH 3.5 with phosphoric acid).

2) With N-[(2S)-3-bromo-2-hydroxypropyl]acetamide

Isobutyl 4-(1,1-dioxido-4-thiomorpholinyl)-3,5-difluorophenylcarbamate (2.5 g, 6.9 mmol) and N-[(2S)-3-bromo-2-hydroxypropyl]acetamide (2.7 g, 13.8 mmol, 2.0 eq) and methanol (0.56 ml, 13.8 mmol, 2.0 eq.) are stirred in acetonitrile (5 ml). A slurry of lithium t-butoxide (1.7 g, 20.7 mmol, 3.0 eq) in THF (5 ml) is prepared and added to the carbamate/acetamide mixture while maintaining a temperature less than 20° C. HPLC indicated formation of title compound. HPLC retention time=1.83 mins (column=Phenomenex IB-SIL Phenyl BD, 150 mm×4.6 mm, flow rate–1.0 ml/min, detection at 254 nm, isocratic elution solvent: 350 ml acetonitirile and 650 ml TEAP pH 3.6 (TEAP pH 3.6=0.7 ml triethylamine in 1 L water adjusted to pH 3.5 with phosphoric acid).

Example 9

(S)—N-[3-(alkyl or arylsulfonyloxy)-2-hydroxypropyl]acetamide

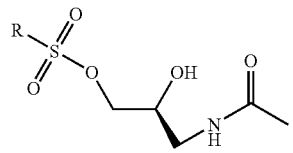

To a mixture of (S)—N-(2,3-dihydroxypropyl)acetamide (1 mmol) and collidene (10 ml) at −40 to 0° C. is added an sulfonylchloride (1 mmol) in which R is aryl or an $C_1$–$C_4$alkyl optionally substituted with one or more of F, Br, Cl, or I. The mixture is stirred at 20–25° C. to give the title compound. (S)—N-(2,3-dihydroxypropyl)acetamide is described by Mbappe et al. in *Tetrahedron Asymmetry* 1993 4(5) 1035–40.

Example 10

(S)—N-[2-(acetyloxy)-3-(alkyl or arylsulfonyloxy)propyl]acetamide

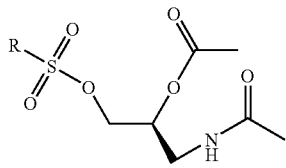

To a mixture of (S)—N-[3-(sulfonyloxy)-2-hydroxypropyl]acetamide from example 9 (1 mmol) and pyridine (5 ml) at −20 to 20° C. is added acetic anhydride (1.25 mmol). The mixture is stirred at 20 to 25° C. to give the title compound.

Example 11

N-[[(5S)-3-[4-(1,1-dioxido-4-thiomorpholinyl)-3,5-difluorophenyl]-2-oxo-5-oxazolidinyl]methyl]acetamide

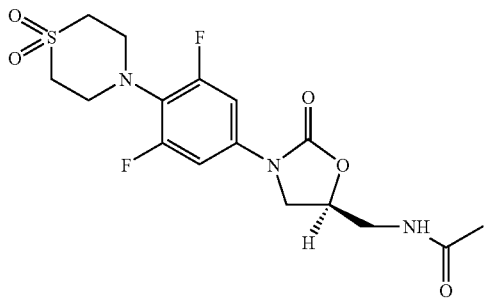

To a mixture of isobutyl 4-(1,1-dioxido-4-thiomorpholinyl)-3,5-difluorophenyl carbamate (100 g, 276 mmol) and (S)—N-[2-(acetyloxy)-3-(sulfonyloxy)propyl]acetamide [Example 10] or (S)—N-[3-(sulfonyloxy)-2-hydroxypropyl]acetamide [Example 9] (552 mmol), THF (60 ml), methanol (17.7 g, 828 mmol, 3.0 eq) and acetonitrile (200 ml) is added a mixture of lithium t-butoxide (66.3 g, 828 mmol, 3.0 eq) and THF (140 ml) over 2 h while maintaining less than 5° C. The mixture is stirred at 14 to 18° C. for 20 h and acetic acid (33.1 g, 552 mmol, 2.0 eq) is added while maintaining less than 20° C., giving the title compound.

What is claimed is:

1. An intermediate of formula IV

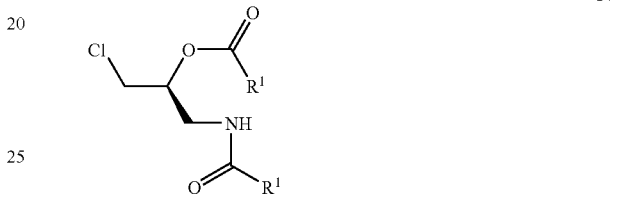

wherein $R^1$ is $CHCl_2$, $CHBr_2$, $CH_2Cl$, $CH_2Br$, $CCl_3$, $CBr_3$, $CHF_2$, or $CF_3$.

2. An intermediate of claim 1 wherein $R^1$ is $CHCl_2$.

* * * * *